United States Patent
Uemura et al.

(10) Patent No.: US 7,163,821 B2
(45) Date of Patent: Jan. 16, 2007

(54) APPLICATION APPARATUS OF 3-DIMENSIONAL KLINOSTAT AND GROWING METHOD USING THE SAME

(75) Inventors: Masaru Uemura, Kobe (JP); Shohei Honda, Kobe (JP); Hiroshi Okazaki, Kobe (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 640 days.

(21) Appl. No.: 10/233,566

(22) Filed: Sep. 4, 2002

(65) Prior Publication Data
US 2003/0041800 A1 Mar. 6, 2003

(30) Foreign Application Priority Data
Sep. 4, 2001 (JP) .............................. 2001-267539

(51) Int. Cl.
C12M 1/36 (2006.01)
(52) U.S. Cl. .............................. 435/286.2; 435/286.7; 435/289.1
(58) Field of Classification Search ..................... None
See application file for complete search history.

(56) References Cited

U.S. PATENT DOCUMENTS 4,874,358 A * 10/1989 Brimhall et al. .............. 494/37
4,988,623 A 1/1991 Schwarz et al.
5,989,913 A 11/1999 Anderson et al.

FOREIGN PATENT DOCUMENTS

| JP | 64-56400 | 3/1989 |
| JP | 6-321700 | 11/1994 |
| JP | 7-89798 | 10/1995 |
| JP | 2000-79900 | 3/2000 |

OTHER PUBLICATIONS

A. McPherson, Journal of Physics D: Applied Physics, vol. 26, No. 8B, XP-000387619, pp. B104-B112, "Virus and Protein Crystal Growth on Earth and in Microgravity", Aug. 14, 1993.
Takayuki Hoson, et al., "Evaluation of the three-dimensional clinostat as a simulator of weightlessness", Planta, vol. 203, 1997, pp. S187-S197.
Brian R. Unsworth, et al., "Growing tissues in microgravity", Nature Medicine, vol. 4, No. 8, Aug. 1998, pp. 901-907.
R. H. Huijser, "Desktop RPM: New Small Size Microgravity Simulator for the Bioscience Laboratory", DESC web site, http://www.desc.med.vu.nl, Aug. 2000, pp. 1-5.
Hans S. Keirstead, "Stem Cell Transplantation Into the Central Nervous System and the Control of Differentiation", Journal of Neuroscience Research, vol. 63, 2001, pp. 233-236.

* cited by examiner

*Primary Examiner*—David Redding
(74) *Attorney, Agent, or Firm*—Oblon, Spivak, McClelland, Maier & Neustadt, P.C.

(57) ABSTRACT

In an application apparatus of a klinostat, an object is encapsulated in a vessel. A rotating unit rotates the vessel around n axes (n is an integer more than 1) such that gravity is equally applied to the object. A fluid supply unit supplies fluid into the vessel, while the vessel is rotated.

16 Claims, 8 Drawing Sheets

APPLICATION APPARATUS OF 3-DIMENSIONAL KLINOSTAT AND GROWING METHOD USING THE SAME

BACKGROUND OF THE INVENTION

1. Field of the Invention

The present invention relates to an application apparatus of a 3-dimensional klinostat and a growing method using the same.

2. Description of the Related Art

A 3-dimensional klinostat is known as an apparatus for distributing the direction of weight applied to a sample into 3-dimensional directions. The 3-dimensional klinostat can set the sample to a quasi-gravity free state by rotating the sample around plural axes, and is used for the growth of animals and plants in the quasi gravity free state. Such a 3-dimensional klinostat is disclosed in Japanese Laid Open Patent Application (JP-P2000-79900A). The conventional 3-dimensional klinostat controls the rotation of the sample to reduce time average gravity applied to the sample to 0.

In case of using the 3-dimensional klinostat, there is a case where the sample must be supplied with fluid. For example, in case of cultivation of a cell in the rotation state, culture fluid must be supplied to the cell. At this time, when the cell is cultivated in the rotation state using the conventional 3-dimensional klinostat, it is necessary to stop the rotation and to replace culture fluid to replace the culture fluid used for the cultivation.

It is desired that the 3-dimensional klinostat is provided which rotates the sample around plural axes and supplies the sample with fluid in the rotation state of the sample.

SUMMARY OF THE INVENTION

An object of the present invention is to provide a 3-dimensional klinostat, which rotates the sample around plural axes and supplies the sample with fluid in the rotation state of the sample.

Another object of the present invention is to provide a cell lump cultivation apparatus which cultivates a cell lump while rotating a cultivation vessel around plural axes and supplies the sample with cultivation fluid in the rotation state of the cultivation vessel.

Another object of the present invention is to provide a cell lump cultivation apparatus which cultivates a cell lump while rotating a cultivation vessel around plural axes and can make a long term cultivation possible.

Another object of the present invention is to provide an organism growing apparatus which grows an organism while rotating an organism growth vessel around plural axes and in which it is possible to supply material necessary to grow up the organism to the organism in the rotation state of the growing vessel.

Another object of the present invention is to provide a material forming apparatus which forms substance from materials while rotating a vessel containing materials around plural axes and in which it is possible to supply the materials or thermal medium as fluid to the vessel in the rotation state of the vessel.

In an aspect of the present invention, an application apparatus of a klinostat, includes a vessel in which an object is encapsulated, a rotating unit which rotates the vessel around n axes (n is an integer more than 1) such that gravity is equally applied to the object, and a fluid supply unit which supplies fluid into the vessel, while the vessel is rotated.

The object is a cell lump, and the cell lump and the fluid is encapsulated in the vessel. At this time, the cell lump may be adhered to an artificial matrix. The fluid, the artificial matrix, and a supporting section for supporting the artificial matrix are encapsulated in the vessel. Also, the fluid contains an agent to promote differentiation of the cell lump. Also, the coefficient of viscosity of the fluid is desirably adjusted such that the cell lump does not touch the vessel.

Also, the fluid supply unit may circulate the fluid. The fluid supply unit may dump the fluid.

Also, when the object is an organism, the fluid supply unit desirably supplies the fluid, which contains material necessary for growth of the organism, into the vessel.

Also, the fluid supply unit has a function to adjust a concentration of at least a gas contained in the fluid.

Also, the support section may have a pipe functioning a vein.

Also, the vessel may include a first room to which the fluid is supplied from the fluid supply unit, a second room in which the object is capsulated, and a separation member which has a plurality of holes and is provided for separation of the first and second rooms, the fluid in the first room and the fluid in the second room are exchanged through the plurality of holes.

In another aspect of the present invention, a 3-dimensional klinostat includes a rotating unit which rotates a vessel around n axes (n is an integer more than 1), and a fluid supply unit which supplies fluid to the vessel in a rotation state of the vessel around the n axes.

The 3-dimensional klinostat may further include a taking-out unit which takes out an object from the vessel.

Also, the fluid supply unit desirably has a material concentration adjusting function to control a concentration of a material contained in the fluid.

In another aspect of the present invention, a 3-dimensional klinostat includes a first member which supports a vessel, a first rotary joint which supports the first member rotatably around a first rotation axis, a first rotating unit which rotates the first member around the first rotation axis, a second member which supports the first rotary joint, a second rotary joint which supports the second member rotatably around a second rotation axis which is not parallel to the first rotation axis, a second rotating unit which rotates the second member around the second rotation axis. The second rotary joint supplies fluid to the vessel through the first rotary joint and the second rotary joint.

In another aspect of the present invention, a cell cultivation apparatus includes a cultivation vessel which accommodates a cultivation cell lump, a rotating unit which rotates the cultivation vessel around n axes (n is an integer more than 1), and a culture fluid supply unit which supplies culture fluid from a stationary system to the cultivation vessel in a rotation state of the cultivation vessel around the n axes.

Also, the cultivation vessel desirably accommodates an artificial matrix to which the cultivation cell lumps are adhered. In this case, the artificial matrix may be fixed on the cultivation vessel.

Also, when the artificial matrix contains an artificial matrix pipe, the culture fluid supply unit supplies the culture fluid through artificial matrix pipe.

Also, the cell cultivation apparatus may further include a culture fluid tank which accumulates the culture fluid discharged from the cultivation vessel. The culture fluid supply apparatus takes out the culture fluid from the culture fluid tank and supplies to the cultivation vessel.

Also, the cell cultivation apparatus may further include a material concentration adjusting unit which controls a concentration of a material contained in the culture fluid.

Also, the cultivation vessel may include a supply pipe through which the culture fluid is supplied from the culture fluid supply unit, a first room which is connected with a discharge pipe through which the culture fluid is discharged, and a second room which is separated from the first room by a separation member for which holes are provided to pass the culture fluid and holds the cultivation cell lump in the culture fluid.

Also, the rotating unit may include a first member which supports the cultivation vessel, a first rotary joint which supports the first member rotatably around a first rotation axis, a first rotating unit which rotates the first member around the first rotation axis, a second member which supports the first rotary joint, a second rotary joint which supports the second member rotatably around a second rotation axis which is not parallel to the first rotation axis, and a second rotating unit which rotates the second member around the second rotation axis. The culture fluid supply unit supplies the culture fluid to the cultivation vessel through the first rotary joint and the second rotary joint.

In another aspect of the present invention, a cell sample forming apparatus includes a cultivation vessel which accommodates a cell, a rotating unit which rotates the cultivation vessel around n axes (n is an integer more than 1), and a fixation liquid supply unit which supplies fixation liquid from a stationary system to the cultivation vessel to fix the cell or a gene of the cell, in a rotation state of the cultivation vessel around the n axes.

In another aspect of the present invention, an organism growing apparatus includes a growth vessel which accommodates an organism, a rotating unit which rotates the growing vessel around n axes (n is an integer more than 1), and a fluid supply unit which supplies fluid, which contains material necessary for growth of the organism in the growth vessel, from a stationary system, in a rotation state of the growth vessel around the n axes.

In another aspect of the present invention, a material forming apparatus includes a vessel which stores raw materials and forms material from the raw materials, a rotating unit which rotates the vessel around n axes (n is an integer more than 1), and a thermal medium supply unit which supplies thermal medium from a stationary system to the vessel for thermal exchange with the vessel in a rotation state of the vessel around the n axes.

In another aspect of the present invention, a material forming apparatus includes a vessel, a rotating unit which rotates the vessel around n axes (n is an integer more than 1), and a raw material supply unit which supplies raw materials of fluid from a stationary system to the vessel in a rotation state of the vessel around the n axes. The vessel forms material from the raw materials.

DESCRIPTION OF THE PREFERRED EMBODIMENTS

Hereinafter, an application apparatus using a 3-dimensional klinostat according to the present invention will be described with reference to the attached drawings. The present invention relates to the U.S. patent application Ser. No. (10/119,895) filed Apr. 11, 2002 and entitled "PROTEIN CRYSTALLIZATION APPARATUS AND PROTEIN CRYSTALLIZATION METHOD". The disclosure of the application is incorporated herein by reference. Also, the present invention relates to a U.S. patent application Ser. No. 10/233,506 entitled "APPLICATION APPARATUS OF 3-DIMENSIONAL KLINOSTAT AND METHOD OF GROWING OBJECT USING THE SAME" and claiming the priority based on Japanese patent application 2001-267539. The disclosure of such application is incorporated herein by reference.

(First Embodiment)

Figure 1:
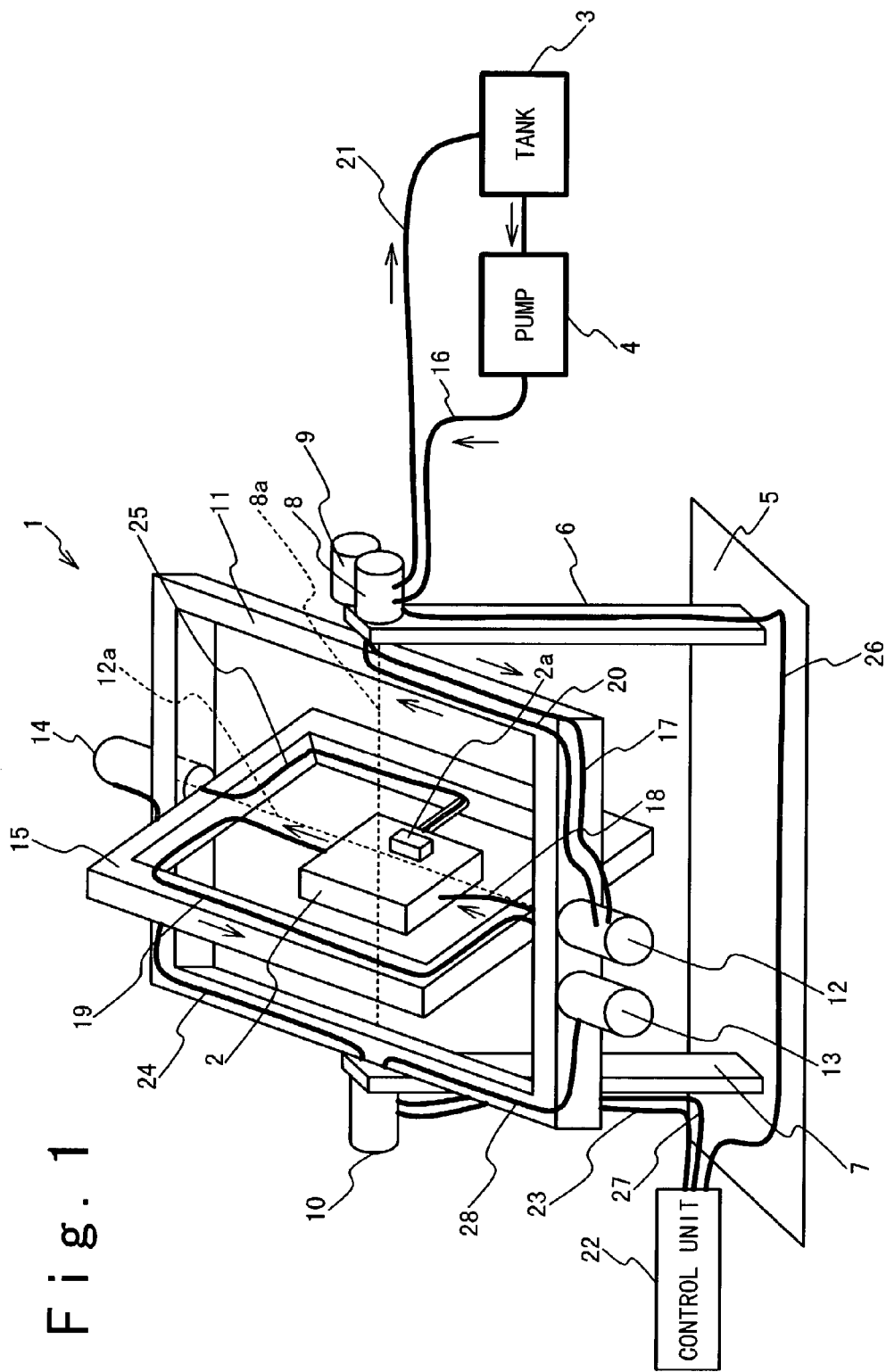
FIG. 1 shows a 3-dimensional klinostat according to a first embodiment of the present invention.

The 3-dimensional klinostat according to the first embodiment of the present invention is used as a part of the cell lump cultivation apparatus. The cell lump cultivation apparatus is comprised of a 3-dimensional klinostat 1 and a cultivation vessel 2, as shown in FIG. 1. Culture fluid and a cultivated cell lump are encapsulated inside the cultivation vessel 2. The cultivated cell lump is not fixed on the cultivation vessel 2 and floats in the culture fluid. A differentiation factor like activin is added to the culture fluid to promote differentiation into the desired tissue. Moreover, it is desirable that a cultivation promotion factor is added to the culture fluid to promote the cultivation.

The 3-dimensional klinostat 1 rotates the cultivation vessels 2 around 2 axes so that the cultivation of the cell lump is carried out in the rotation state to distribute the gravity direction. When the cultivation vessel 2 is rotated around the 2 axes, the gravity direction applied to the cultivation cell lump encapsulated in the cultivation vessel 2 is distributed. Thus, each cell lump can be cultivated to all the directions, and the cultivation of the cultivation cell lump in the 3-dimensional direction becomes possible. Also, through distribution of the gravity direction, the shearing stress by the flow in the cultivation vessel 2 becomes small, and the separation and isolation of the cultivation cell lump are prevented. In this way, the tissue having the 3-dimensional structure is formed by cultivating the cell lump in the rotation state of the cultivation vessel 2 around the 2 axes.

A monitoring unit 2a is connected with the cultivation vessel 2. The monitoring unit 2a monitors the state of the cultivation vessel 2. As the monitoring object, the temperature and pH of the culture fluid in the cultivation vessel 2, the concentrations of oxygen and carbon dioxide and the cultivation state of the cell lump are exemplified.

The tank 3 and the pump 4 are connected with the 3-dimensional klinostat 1 to supply the culture fluid from a stationary system to the cultivation vessel 2. The tank 3 accumulates the culture fluid which should be supplied to the cultivation vessel 2. The pump 4 supplies the culture fluid accumulated in the culture fluid tank 3 to the cultivation vessel 2. The culture fluid is supplied to the cultivation vessel 2 and is returned in the culture fluid tank 3. Thus, the culture fluid to cultivate the cell lump is circulated. The necessary quantity of the culture fluid is restrained by the recirculation of the culture fluid.

It is desirable that the tank 3 has the gas concentration adjusting function to control the concentration of gas contained in the culture fluid. The optimization of the concentrations of the oxygen and the carbon dioxide contained in the culture fluid is important in case of the cultivation of the cell lump. By adjusting the concentrations of the gases contained in the culture fluid, especially, oxygen and carbon dioxide, it is possible to cultivate the cell lump in the more desirable environment. Specifically, the tank 3 is formed of gas replaceable material and an atmosphere around the tank 3 is adjusted. Thus, the gas contained in the culture fluid can be controlled to a desired concentration.

The structure of the 3-dimensional klinostat 1 will be describes below in detail. The 3-dimensional klinostat 1 is comprised of a main unit 5 which is installed in a stationary system. The main unit 5 is joined to a support 6 and a support 7. A rotary joint 8 and a motor 9 are joined to the support 6. An electric slip ring 10 is joined to the support 7. The rotary joint 8 and the electric slip ring 10 rotatably support an outer frame 11. The motor 9 drives the outer frame 11 through a power communication mechanism (not shown) such as gears and a belt and rotates the outer frame 11 around the rotation axis 8a. Also, the rotary joint 12, the motor 13 and the electric slip ring 14 are joined to the outer frame 11. The rotary joint 12 and the electric slip ring 14 rotatably support an inner frame 15. The motor 12 drives the inner frame through a power communication mechanism (not shown) such as gears and a belt and rotates the inner frame 14 around the rotation axis 12a.

The inner frame 15 is connected with the above-mentioned cultivation vessel 2. The cultivation vessel 2 is located in the neighborhood in the intersection of the rotation axes 8a and the rotation axis 12a. The cultivation vessel 2 is rotated together with the inner frame 15. When the outer frame 11 and the inner frame 15 are rotated respectively, the cultivation vessel 2 is rotated around the 2 axes.

A control system 22 is provided for the stationary system is connected with the 3-dimensional klinostat 1. The electric power is supplied to the above-mentioned monitoring unit 2a, the motor 9 and the motor 13 from the control system 22. Also, the monitoring unit 2a, the motor 9 and the motor 13 are controlled by the control system 22. The data acquired by the monitoring systems 2a is displayed on a monitor (not shown) contained in the control system 22. More detailed, the electric cable 23, the electric slip ring 10, the electric cable 24, the electric slip ring 14 and the electric cable 25 supplies the electric power from the control system 22 to the monitoring unit 2a, and exchange signals between the control system 22 and the monitoring unit 2a. The electric slip ring 10 is connected with the control system 22 through the electric cable 23. The outer frame 11 and the electric cable 23 are electrically connected through the electric slip ring 10 rotating together with the electric cable 24. The inner frame 15 and the electric cable 24 are electrically connected through the electric slip ring 14 rotating together with the electric cable 25. The electric cable 25 is connected with the monitoring unit 2a. The monitoring unit 2a operates with the electric power supplied through the electric cable 25 and signals exchange with the control systems 22 via the electric cable 25.

Also, the electric cable 26 is connected with the motor 9 joined to the support 6. The electric cable 26 supplies the electric power from the control system 22 to the motor 9 and helps the signal exchange between the control system 22 and the motor 9. The motor 9 rotates the outer frame 11 with the electric power supplied through the electric cable 26. The electric cable 27, the electric slip ring 10 and the electric cable 28 supplies the electric power from the control system 22 to the motor 13 joined to the outer frame 11 and helps the exchange of signals between the control system 22 and the motor 13. The electric slip ring 10 is connected with the control system 22 through the electric cable 27. The electric cable 27 are electrically connected through then power slip ring 10 with the electric cable 28 rotating together with the outer frame 11. The electric cable 28 is connected with the motor 13. The motor 13 rotates the inner frame 15 with the electric power supplied through the electric cable 28.

It should be noted that in FIG. 1, each of the electric cables 23 to 28 is shown as a single line. However, each of the electric cables 23 to 28 is a set of electric cables of a necessary number.

The supply of the culture fluid from the pump 4 to the cultivation vessel 2 is carried out through the rotary joint 8 and the rotary joint 12. The fresh culture fluid sent from the pump 4 reaches the rotary joint 8 through the supply pipe 16. The rotary joint 8 introduces the culture fluid into the supply pipe 17 rotating with the outer frame 11. The rotary joint 12 is connected with supply pipe 17 and introduces the culture fluid into the inner frame 15 rotating with the supply pipe 18. The supply pipe 18 is connected with the cultivation vessel 2 and the culture fluid is supplied to the cultivation vessel 2 from the supply pipe 18.

In the same way, the discharge of the culture fluid from the cultivation vessel 2 to the tank 3 is carried out through the rotary joint 8 and the rotary joint 12. The cultivation vessel 2 discharges the culture fluid to discharge pipe 19. The culture fluid discharged to the discharge pipe 19 is introduced into the discharge pipe 20 rotating with the outer frame 11 through the rotary joint 12. The culture fluid introduced into the discharge pipe 20 is introduced through the rotary joint 12 into the discharge pipe 21 which is located on the stationary system. The culture fluid introduced into the discharge pipe 21 is returned to the tank 3.

Figure 2:
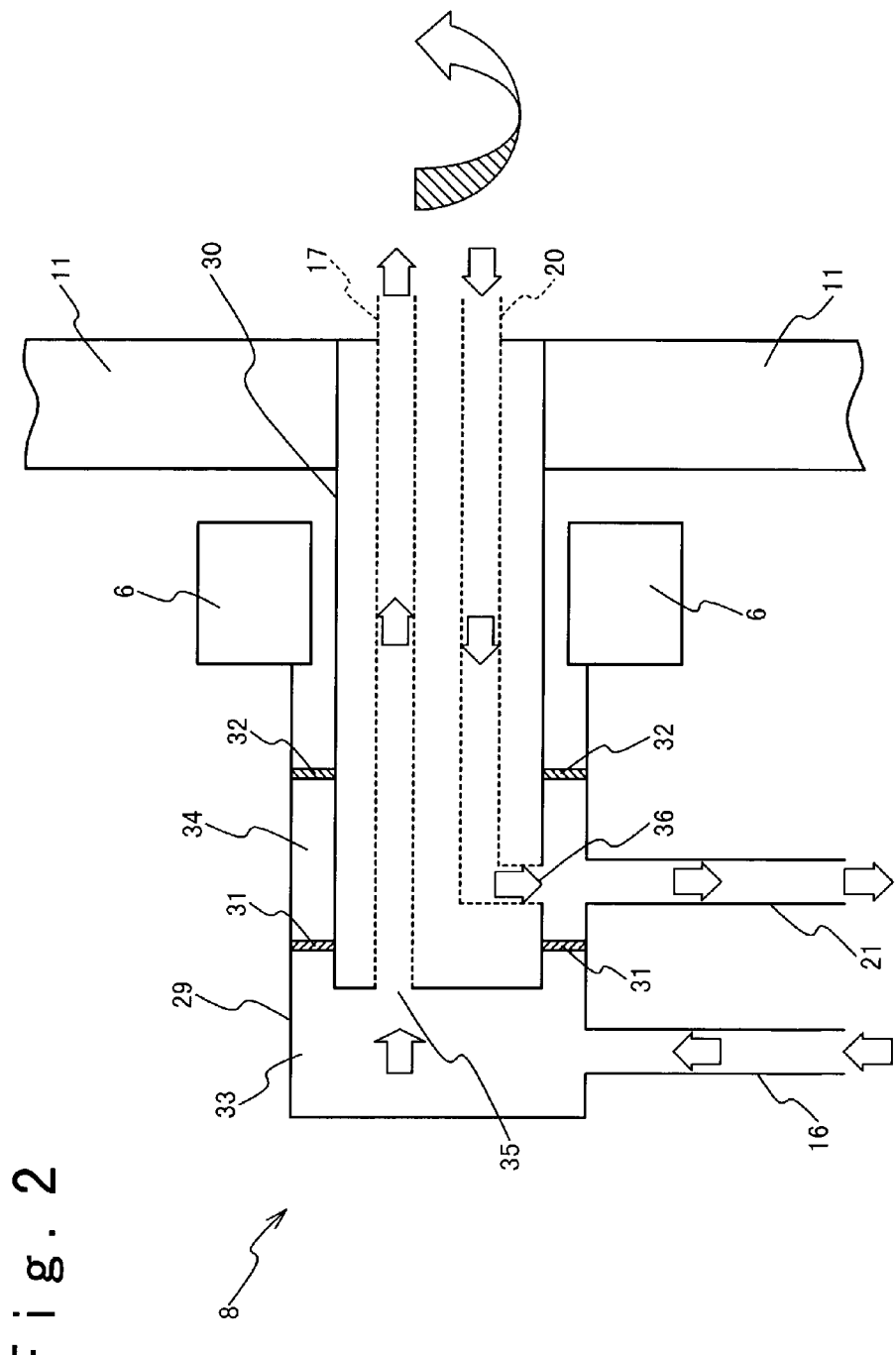
FIG. 2 is a diagram showing the structure of a rotary joint.

FIG. 2 shows the rotary joint 8 in detail. The rotary joint 8 contains a fixation section 29 and a rotation section 30. The fixation section 29 and the rotation section 30 have column bodies with different diameters and the rotation section 30 is rotatably inserted in the fixation section 29. The fixation section 29 is attached to the support 6 and the rotation section 30 is attached to the outer frame 11. In the space between the fixation section 29 and the rotation section 30, a first liquid introduction room 33 and a second liquid introduction room 34 are formed by seals 31 and 32. The first liquid introduction room 33 and the second liquid introduction room 34 are separated by the seal 31. The seal of the second liquid introduction room 34 from the external is kept by the seal 32. The supply pipe 16 connected with the pump 14 is connected with the first liquid introduction room 33. The discharge pipe 21 connected with the tank 3 is connected with the second liquid introduction room 34.

A first hole 35 opened in the first liquid introduction room 33 and a second hole 36 opened in the second liquid introduction room 34 are provided for the rotation section 30. The first hole 35 is connected with the above-mentioned supply pipe 17 which is fixed to the external frame 11. The second hole 36 is connected with the discharge pipe 20 which is fixed to the external frame 11. The rotary joint 8 having the above structure connects the supply pipe 16 and the supply pipe 17 and the discharge pipe 20 and the discharge pipe 21 regardless of the angle between the support 6 and the outer frame 11. Also, the rotary joint 12 has the same structure as the rotary joint 18, and connects the supply pipe 17 and the supply pipe 18 and the outer frame 11 and the inner frame 15 regardless of the angle between the discharge pipe 19 and the discharge pipe 20.

In this way, the culture fluid is supplied to the cultivation vessel 2 through the rotary joint 18 and the rotary joint 12 from outside the 3-dimensional klinostat 11. Moreover, the culture fluid is discharged from the cultivation vessel 2 outside the 3-dimensional klinostat 11.

When the culture fluid is supplied to the cultivation vessel 2 from the external, the disorder of the liquid flow can generate inside the cultivation vessel 2 because the culture fluid flows. The disorder of the liquid flow induces the dispersion of the cell lump and obstructs the growth of a 3-dimensional tissue. In order to prevent this, the cultivation vessel 2 has the structure such that an influence due to the disorder of the liquid flow is restrained.

Figure 3:
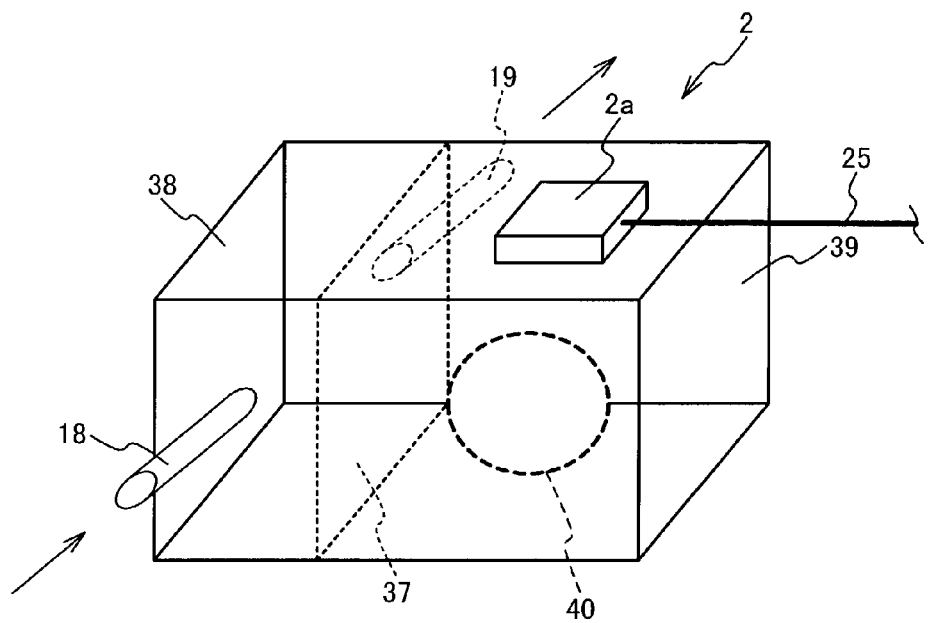
FIG. 3 is a diagram showing the structure of a cultivation vessel.

FIG. 3 shows the cultivation vessel 2. The inside of the cultivation vessel 2 is separated into a flow path room 38 and the cultivation room 39 by an exchange film 37. The supply pipe 18 which supplies the culture fluid, and the discharge pipe 19 which discharges the culture fluid are connected with the flow path room 38. Holes are provided for the exchange film 37. Through the holes, the culture fluid diffuses from the flow path room 38 to the cultivation room 39, and the culture fluid is exchanged between the flow path room 38 and the cultivation room 39. The cell lump 40 is put in the floating state in the cultivation room 39 and the cultivation of the cell lump 40 is carried out inside the cultivation room 39.

In the cultivation vessel 2 having the above structure, the culture fluid does not flow directly into the cultivation room 39 where the cultivation of the cell lump 40 is carried out. Thus, the influence of the disorder of the liquid flow caused for the culture fluid to flow into the cultivation vessel 2 on the cultivation of cell lump 40 is restrained.

As described above, in the cell lump cultivation apparatus in this embodiment, the culture fluid is supplied from the tank 3 to the cultivation vessel 2 and discharged from the cultivation vessel 2, while the cultivation vessel 2 is rotated. Also, the culture fluid in the cultivation vessel 2 can be replaced. Thus, the cell lump cultivation apparatus makes the cultivation of the cell lump for a long-term possible, and especially it is used in artificial organ manufacture. When it is tried to manufacture an artificial organ, the cell lumps for the artificial organ must be cultivated for a long term. In the cell lump cultivation apparatus, the culture fluid is supplied from the stationary system to the cultivation vessel 2 through the rotary joints 8 and 10, and the culture fluid can be replaced without stopping the rotation of the cultivation vessel 2.

Moreover, the cell lump cultivation apparatus is used for the confirmation of the form of the cell lump under the rotation environment and the cultivation state of a gene. In this case, fixation liquid like glutaraldehyde is put in the tank 3 instead of the culture fluid. A method of confirming the cultivation situation of a DNA under the rotation environment using the cell lump cultivation apparatus will be described in detail. First, the cell lump as the object of the confirmation of the form of the cell lump under the rotation environment or the cultivation situation of the gene is cultivated in the rotation state of the cultivation vessel 2 around the 2 axes. When the fixation liquid accommodated in the tank 3 is supplied to the cultivation vessel 2 in the rotation state of the cultivation vessel 2 around the 2 axes. When fixation liquid is supplied to the cultivation vessel 2, the form of the cell lump and/or the gene of the cell lump put in the cultivation vessel 2 is fixed in accordance with the component of fixation liquid. A sample to confirm the form of the cell lump and/or the cultivation of the gene is formed. The sample is observed and analyzed, and the form of the cell lump and the present situation of the gene in the rotation environment are observed.

In this way, by confirming the form of the cell lump and the present situation of the gene, the form of the cell lump and the present situation of the gene under the rotation environment can be more precisely confirmed. The form of the cell lump and the present situation of the gene sometimes change within several seconds. When the cell lump and the gene are fixed after stopping the rotation temporarily, there is possibility that the form of the cell lump and the present situation of the gene change during a taking-out operation. In above-mentioned method, the fixation of the cell lump and the gene is carried out while the rotation is carried out. The present situation of the gene and the form of the cell lump under the rotation environment can be more correctly confirmed.

It should be noted that the culture fluid used for the cultivation is circulated in the first embodiment. However, the culture fluid discharged from the cultivation vessel 2 may be dumped away just as it is. In this case, the discharge pipe 28 used when the culture fluid is discharged from the cultivation vessel 2 is not connected with the tank 3.

Also, in the first embodiment, the cultivation vessel 2 is rotated around the 2 axes. However, the cultivation vessel 2 may be rotated around more axes than 2 axes.

(Second Embodiment)

In the cell lump cultivation apparatus according to the second embodiment of the present invention, the cultivation vessel filled with the culture fluid is rotated around the 2 axes. The second embodiment is the same as the first embodiment in the point that a cell lump is cultivated inside the cultivation vessel. In the second embodiment, the gravity is applied 3-dimensionally, like the first embodiment. Thus, the 3-dimensional cultivation that the cell lump is adhered uniformly to the artificial matrix with a 3-dimensional structure becomes possible. Also, the shearing force due to the fluid stirring caused in the rotation of the cultivation vessels around the 2 axes rotated is small, so that the separation and damage of the adhered and densified cell lumps can be prevented.

In the second embodiment, a cell lump is cultivated in the state adhered to the artificial matrix which is fixed to the cultivation vessel to be adaptable to the manufacture of the artificial organ. In order to form a large-sized artificial organ, it is necessary to cultivate a large-sized cell lump. However, it is difficult to keep a large-sized cell lump at a full floating state and it is easy for damage to be added to the cell lump when the cell lump is large sized. Since the cell lump is cultivated on the artificial matrix which is fixed on the cultivation vessel, the damage of the cell lump is prevented and the cultivation of the large-sized cell lump becomes possible. At this time, the artificial matrix supports the cell lump fixedly, becomes the skeleton of the cultivation of the cell lump and forms a part of the artificial organ.

Figure 4:
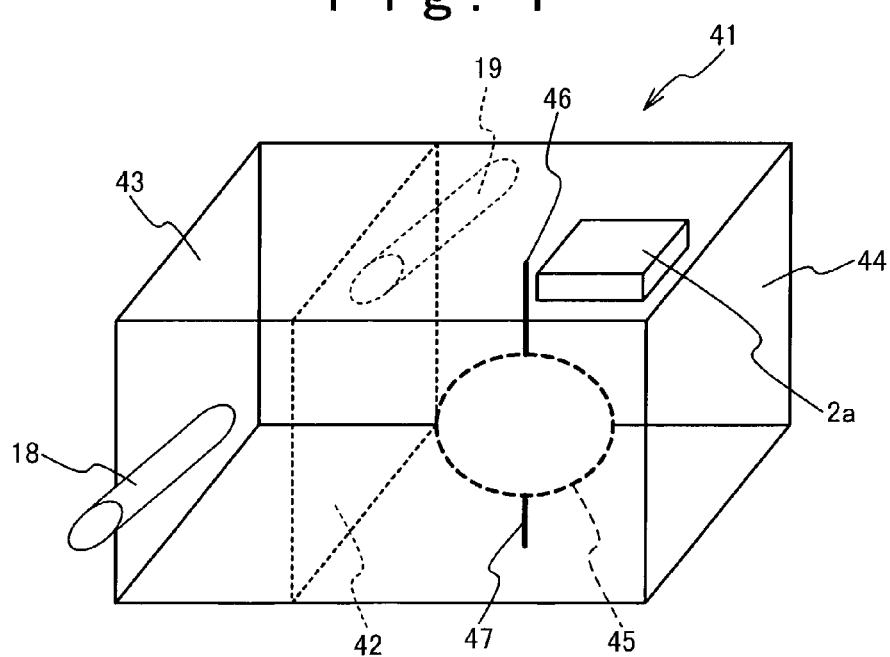
FIG. 4 is a diagram showing the structure of a cultivation vessel used in the second embodiment of the present invention.

In detail, in the second embodiment, the cultivation vessel 41 shown in FIG. 4 is used instead of the cultivation vessel 2 in the first embodiment. A monitoring unit 2a is provided for the cultivation vessel 41 to monitor the state of the cultivation vessel 41 like the cultivation vessel 2. As mentioned above, the electric power is supplied to the monitoring unit 2a through the electric slip rings 10 and 14. The cultivation vessel 41 is separated into a flow path room 43 and a cultivation room 44 by an exchange film 42. The supply pipe 18 which supplies the culture fluid and the discharge pipe 19 which discharges the culture fluid are connected with the flow path room 43. Holes are provided for the exchange film 42, and through the holes, the diffusion of the culture fluid from the flow path room 43 to the cultivation room 44 and the exchange of the culture fluid between the flow path room 43 and the cultivation room 44 are carried out.

An artificial matrix 45 and artificial matrix support sections 46 and 47 are stored in the cultivation room 44. For example, the artificial matrix 45 is formed of sponge collagen. The artificial matrix 45 becomes the skeleton when a cell lump (not shown) is cultivated and the cell lump is cultivated in the state adhered to the artificial matrix 45. The artificial matrix support sections 46 and 47 hold the artificial matrix 45 fixedly at the wall of the cultivation vessel 41. The cell lump to be cultivated is fixedly supported in the culture fluid by the artificial matrix 45 and the artificial matrix support sections 46 and 47.

Another structure of the cell lump cultivation apparatus according to the second embodiment of the present invention is the same as that of the first embodiment and the detailed description is not carried out.

In the second embodiment, the cultivation of the cell lump is carried out as follows. The cultivated cell lump is adhered to the artificial matrix 45. The artificial matrix 45 is fixed on the wall of the cultivation room 44 by the artificial matrix support sections 46 and 47, and the cultivation vessel 41 is filled with the culture fluid. The cultivation vessel 41 is rotated around the 2 axes by the 3-dimensional klinostat 11 and the cultivation is started. The culture fluid accumulated in the tank 3 is supplied to the cultivation vessel 41 through the rotary joint 8 and the rotary joint 12 during the cultivation. Also, the culture fluid discharged from the cultivation vessel 41 is recycled to the tank 3 through the rotary joint 12 and the rotary joint 8. The culture fluid flows in the cultivation room 44 3-dimensionally and gravity is applied to the artificial matrix 45 from all directions. Thus, the cell lump is cultivated 3-dimensionally on the surface of the artificial matrix 45.

Figure 5:
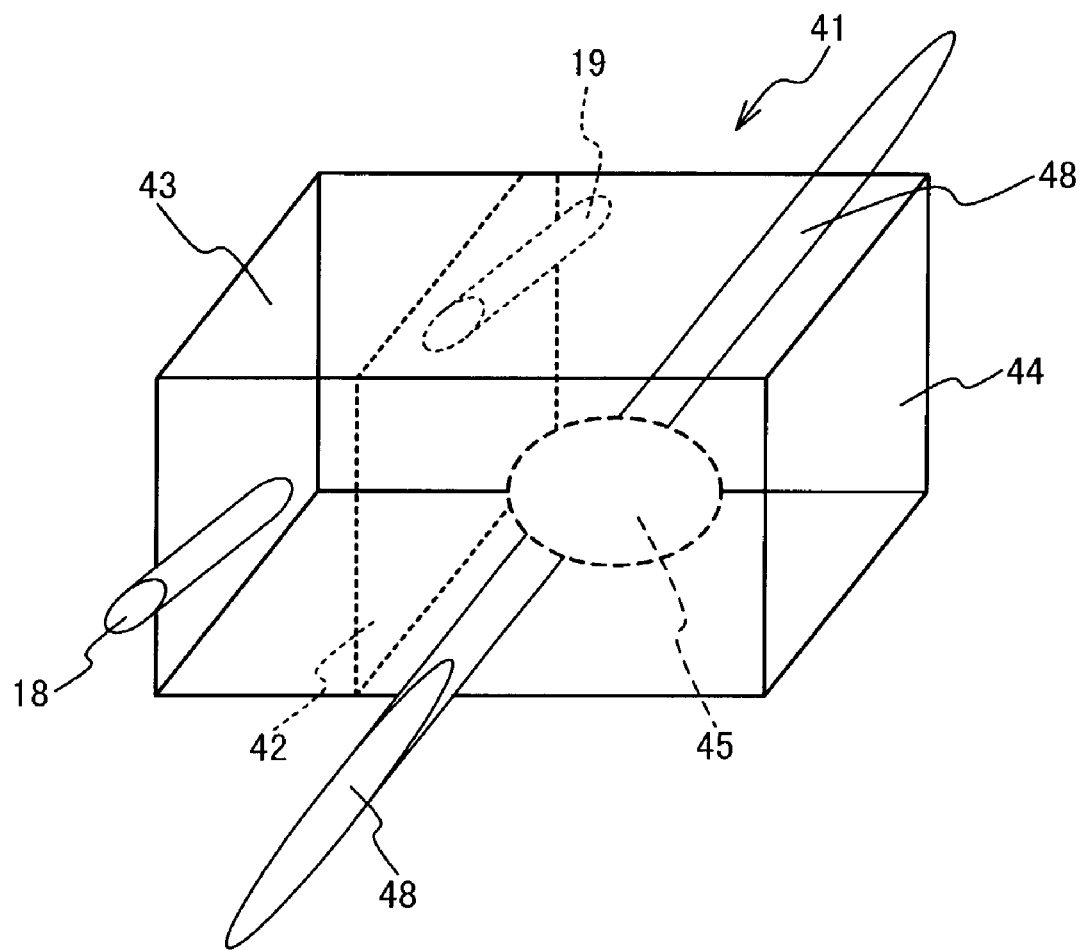
FIG. 5 is a diagram showing the structure of a modification of the cultivation vessel.

The tissue formed of the cultivation cell lump and the artificial matrix 45 is taken out from the cultivation vessel 41 as the artificial organ. The regeneration and recovery of the internal organs are possible by transplanting the artificial organ into a body or installing it out of the body. It is desirable that an artificial matrix pipe 48 may be provided for the artificial matrix 45 in order to form a large-sized artificial organ, as shown in FIG. 5. The one end of the artificial matrix pipe 48 is connected with the supply pipe 18 shown in FIG. 1, and the other end is connected with the discharge pipe 19, and the culture fluid is passed through the artificial matrix pipe 48. At this time, when the tissue formed on the artificial matrix 45 is large sized, it is difficult to supply the material necessary for multiplication of the tissue. The artificial matrix pipe 48 through which the culture fluid flows acts as an artificial vein and the material necessary for multiplication is supplied into the tissue. When the artificial matrix pipe 48 is provided, the artificial matrix pipe 48 can support the artificial matrix 45. As shown in FIG. 5, the artificial matrix support sections 46 and 47 do not have to be always provided.

In the cell lump cultivation apparatus in the second embodiment, the culture fluid is supplied from the tank 3 to the cultivation vessel 2 and is discharged from the cultivation vessel 2, while the cultivation vessel 2 is rotated, like the first embodiment. Moreover, the culture fluid in the cultivation vessel 2 can be exchanged. Also, in the second embodiment, the cell lump is cultivated on the fixed artificial matrix 45 and it is possible to form a large-sized tissue. In this point, the cell lump cultivation apparatus in the second embodiment is especially applied to manufacture an artificial organ.

(Third Embodiment)

The 3-dimensional klinostat according to the third embodiment of the present invention is used as a part of a plant growing apparatus. The plant growing apparatus in the third embodiment rotates a growth vessel which accommodate a plant around the 2 axes and the gravity applied to the plant as the growth object is distributed into 3-dimensional directions. The plant growing apparatus in the third embodiment is used to confirm the physiological activity of the plant under the environment the gravity is distributed 3-dimensionally.

The plant growing apparatus in the third embodiment which rotates the growth vessels around the 2 axes has the same structure as the cell lump cultivation apparatus in the first embodiment approximately but is different from the first embodiment on the following points.

Figure 6:
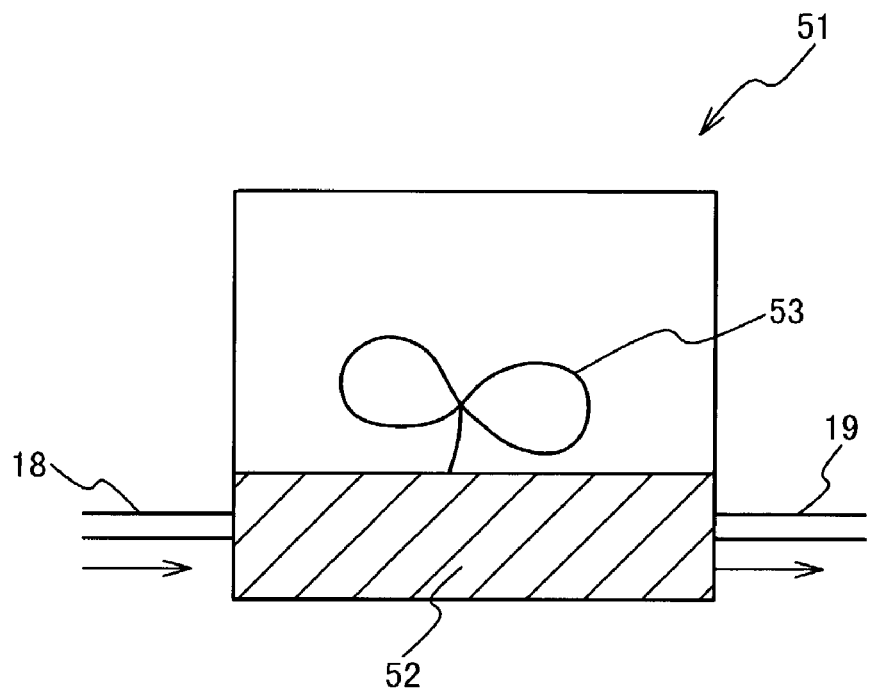
FIG. 6 is a diagram showing the structure of a growth vessel 51 used in the third embodiment of the present invention.

The growth vessel 51 shown in FIG. 6 is first used instead of the cultivation vessel 2 used in the first embodiment. The growth plant is accommodated in the growth vessel 51. The details of the growth vessel 51 are later mentioned.

Second, not the culture fluid but growth liquid is accumulated in the tank 3 shown in FIG. 1. The growth liquid is controlled to contain the material necessary to grow a plant. The growth liquid accumulated in the tank 3 is supplied to the growth vessel 41 through the rotary joint 8 and the rotary joint 12. The excessive growth liquid is discharged from the growth vessel 41 and is discharged to the tank 3 through the rotary joint 8 and the rotary joint 12. It is desirable that the tank 3 has the function to adjust the concentration of the material necessary to grow the plant the oxygen concentration and pH of growth liquid.

As shown in FIG. 6, the above-mentioned growth vessel 51 is connected with a supply pipe 18 and a discharge pipe 19. The growth liquid is supplied from the supply pipe 18 to the growth vessel 51 and the excessive growth liquid is discharged from the discharge pipe 19. The growth vessel 51 has a water keeping member 52 like lock wool therein. The growth liquid supplied to the growth vessel 51 is filtered into the water keeping member 52. The plant 53 as the growing object is planted in the water keeping member 52, and the plant 53 absorbs the material necessary to grow from the growth liquid filtered into the keeping member 52.

The plant growing apparatus in the third embodiment supplies the growth liquid to the growth vessel 51 in the state which the growth vessels 51 is rotated around the 2 axes, and discharges the growth liquid from the growth vessel 51, so that the growth liquid in the growth vessel 51 can be exchanged. The plant growing apparatus is not needed to stop the rotation of the growth vessel 51 to supply, discharge or exchange the growth liquid to the growth vessel 51 and is suitable to grow a plant under the rotation environment for a long term.

It should be noted that in the third embodiment, the growth vessel 51 is rotated around the 2 axes. However, the growth vessel 51 may be rotated around two or more axes.

Also, the plant growing apparatus in the third embodiment can be applied to the growth of a microorganism like mold. In this case, the microorganism is stored in the growth vessel 51 instead of plant 53 and is grown.

(Fourth Embodiment)

The 3-dimensional klinostat according to the fourth embodiment of the present invention is used as a part of an aquatic organism growing apparatus. The aquatic organism growing apparatus in the fourth embodiment rotates the growth vessel accommodating the aquatic organism as the growth object around the 2 axes. The gravity applied to the aquatic organism as the growth object is distributes in all the directions 3-dimensionally. The aquatic organism growing apparatus in the fourth embodiment is used to confirm the activated course of the physiological activity of the aquatic organism under the environment in which the gravity is distributes in all the directions 3-dimensionally.

The aquatic organism growing apparatus in the fourth embodiment has substantially the same structure as the cell lump cultivation apparatus in the first embodiment and differs from the first embodiment in the following points.

Figure 7:
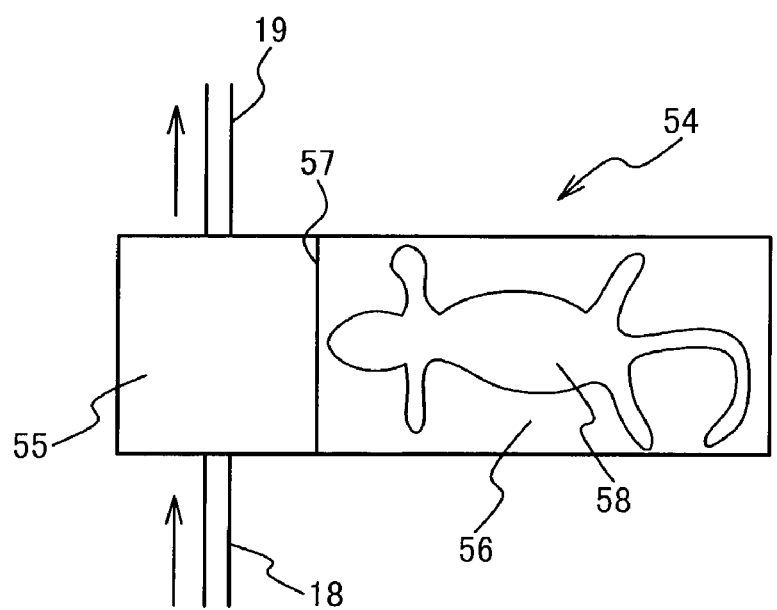
FIG. 7 is a diagram showing the structure of a growth vessel 54 used in the fourth embodiment of the present invention.

First, the growth vessel 54 shown in FIG. 7 is used instead of the cultivation vessel 2 in the first embodiment. The aquatic organism is accommodated in the growth vessel 54. It is desirable that the aquatic organism to be grown may be any of an animal, a plant and a microorganism, e.g., a newt, a fish, a aquatic plant. The details of the growth vessel 54 are mentioned later.

Second, breeding water is accumulated in the tank 3 shown in FIG. 1 instead of the culture fluid. The breeding water is controlled to contain the material necessary to grow the aquatic organism. When the aquatic organism is an animal, the bait of the aquatic organism is mixed with the breeding water and is supplied to the growth vessel 54. The breeding water is accommodated in the tank 3 and is supplied to the growth vessel 54 through the rotary joint 8 and the rotary joint 12. The excessive breeding water is discharged from the growth vessel 54 and is discharged to the tank 3 through the rotary joint 8 and the rotary joint 12. It is desirable that the tank 3 has a gas exchange function to adjust the gas concentration of the breeding water, a control function of pH, and a removal function to remove egesta from the aquatic organism.

As shown in FIG. 7, the above-mentioned growth vessel 54 contains a flow path room 55 and a growth room 56. The supply pipe 18 which supplies the breeding water and the discharge pipe 19 which discharges the breeding water are connected with the flow path room 55. The flow path room 55 is separated from the growth room 56 by a separation member 57. A lot of holes are provided for the separation member 57. Through the holes, the exchange of the culture fluid between the flow path room 55 and the growth room 56 is carried out. The aquatic organism 58 is put in the growth room 56 and the cultivation for the growth of the aquatic organism 58 is carried out in the growth room 56.

Figure 8:
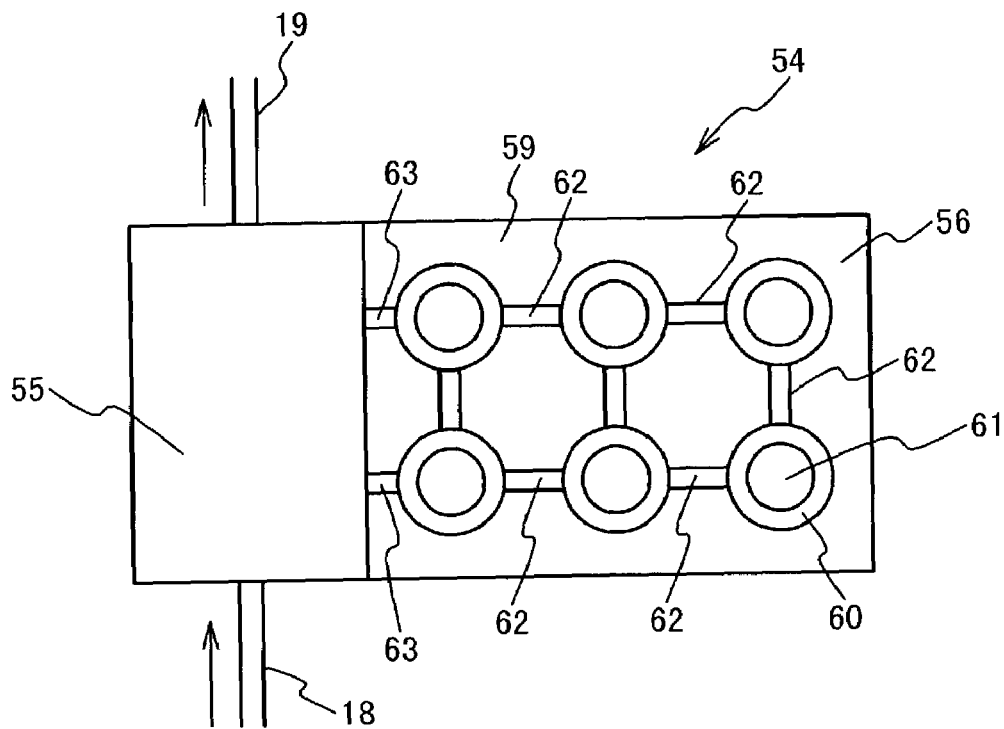
FIG. 8 is a diagram showing the structure of a modification of a growth vessel.

When eggs of the aquatic organism 58 are grown, an egg holder 59 is preferably stored in the growth room 56, as shown in FIG. 8. A plurality of egg storage rooms 60 which are cylindrical holes are provided for the egg holder 59, and the eggs 61 are stored in the egg storage rooms 60 and are fixed therein. Neighbor egg storage rooms 60 are connected with each other by flow paths 62, and the flow path 63 is provided for ones of the egg storage room 60 which face to the flow path room 55 and connected with the flow path room 55. The breeding water is supplied to each egg storage room 60 through the flow path 62 and the flow path 63.

The aquatic organism growing apparatus in the fourth embodiment supplies the breeding water to the growth vessel 54 and discharges from the growth vessel 54, in the rotation state of the growth vessels 54 around of the 2 axes, so that the breeding water in the growth vessel 54 can be exchanged. The aquatic organism growing apparatus needs not to stop the rotation of the growth vessel 54 to supply the breeding water to the growth vessel 54. Therefore, it is suitable to grow the aquatic organism for a long term under the rotation environment.

It should be noted that in the fourth embodiment, the growth vessels 54 are rotated around the 2 axes. However, the growth vessel 54 can be rotated around 2 or more axes.

(Fifth Embodiment)

The 3-dimensional klinostat according to the fifth embodiment of the present invention is used as a part of the animal growing apparatus. The animal growing apparatus in the fifth embodiment rotates the growth vessel, which accommodates an animal as an growth object, around the 2 axes to distribute the direction of the gravity applied to the animal as the growth object 3-dimensionally. The animal growing apparatus in the fifth embodiment is used to confirm the activated course of the physiological activity of the animal under the environment in which the direction the gravity is distributed 3-dimensionally.

The animal growing apparatus in the fifth embodiment, which rotates the growth vessel around the 2 axes, has substantially the same structure as the cell lump cultivation apparatus in the first embodiment but differs from the first embodiment in the following points.

Figure 9:
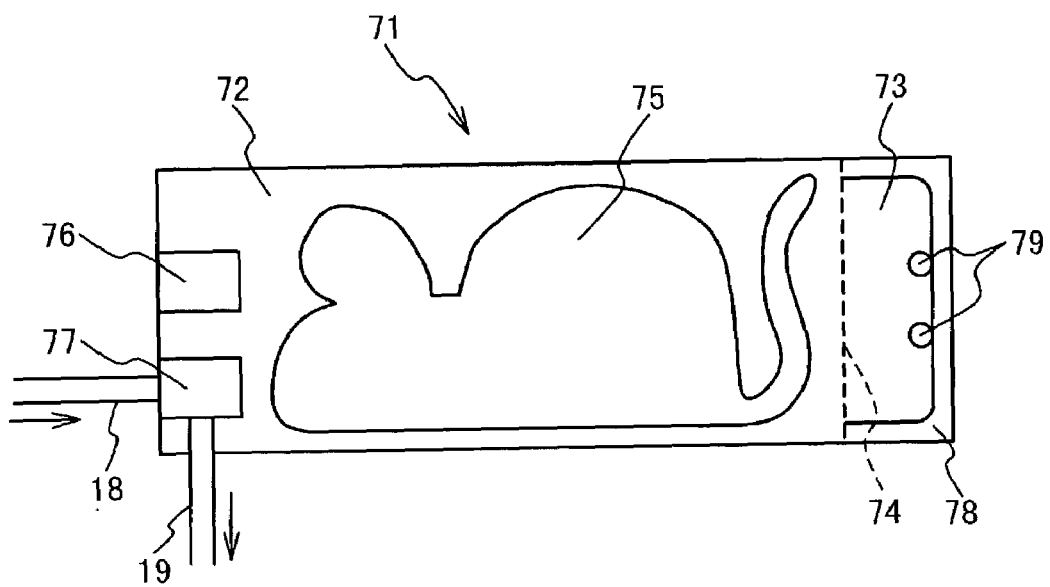
FIG. 9 is a diagram showing the structure of a growth vessel 71 used in the fifth embodiment of the present invention.

First, the growth vessel 71 shown in FIG. 9 is used instead of the cultivation vessel 2 used in the first embodiment. An animal to be grown, e.g., a mouse is housed in the growth vessel 71. The details of the growth vessel 71 are later mentioned.

Second, it is not the culture fluid but drinking water that is accumulated in the tank 3 shown in FIG. 1. The drinking water accumulated in the tank 3 is supplied to the growth vessel 71 through the rotary joint 8 and the rotary joint 12.

Third, a discharge pipe 21 is not connected with the tank 3. The old drinking water after being supplied to the growth vessel 71 is discharged to the discharge pipe 21 through the rotary joint 12 and the rotary joint 8. The drinking water is discharged to the discharge pipe 21 and is dumped away just as it is.

As shown in FIG. 9, a growth room 72 and an excrement processing room 73 are provided for the above-mentioned growth vessel 71. The growth room 72 accommodates the animal 75 as a growth object. It is desirable that the growth room 72 has such a size as the animal 75 cannot change the direction of itself. A bait box 76 and a drinking water supply vessel 77 are provided for the growth room 72. The bait box 76 supplies the bait to the animal 75. The drinking water supply vessel 77 is connected with the supply pipe 18. As described above, the supply pipe 18 is connected with the tank 3 through the rotary joint 8 and the rotary joint 12. The supply pipe 18 supplies the drinking water accumulated in the tank 3 to the drinking water supply vessel 77. The drinking water supply vessel 77 supplies the drinking water supplied from the supply pipe 18 to the animal 75. Also, the drinking water supply vessel 77 is connected with the discharge pipe 19. The old drinking water after being supplied to the drinking water supply vessel 77 is discharged from the discharge pipe 19 through the rotary joint 12 and the rotary joint 8 to the discharge pipe 21. The drinking water is discharged to the discharge pipe 21 and is thrown or dumped away just as it is. The growth room 72 is separated from the excrement processing room 73 by a network 74.

An adhesive sheet 78 and a moisture absorbing member 79 are provided for the excrement processing room 73. The adhesive sheet 78 captures the shit discharged from the animal 75. The moisture absorbing member 79 absorbs urine discharged from the animal 75. The sanitary state of the growth room 72 is maintained by the adhesive sheet 78 and the moisture absorbing member 79.

The animal growing apparatus described above in the fifth embodiment supplies drinking water to the growth vessel 71 in the rotation state of the growth vessels 71 around the 2 axes, and discharges the drinking water from the growth vessel 71, so that the drinking water supplied to the growth vessel 71 can be exchanged. The animal growing apparatus needs not to stop the rotation of the growth vessel 71 to supply drinking water to the growth vessel 71 and to discharge or to exchange. It is suitable to grow the animal for a long term under the rotation environment.

It should be noted that in the fifth embodiment, the growth vessels 71 are rotated around the 2 axes but the growth vessel 71 can be rotated around two or more axes.

(Sixth Embodiment)

The 3-dimensional klinostat according to sixth embodiment of the present invention is used as a part of a sphere material forming apparatus. The sphere material forming apparatus in the sixth embodiment has substantially the same structure as the cell lump cultivation apparatus in the first embodiment but differs from the first embodiment in the following points.

Figure 10:
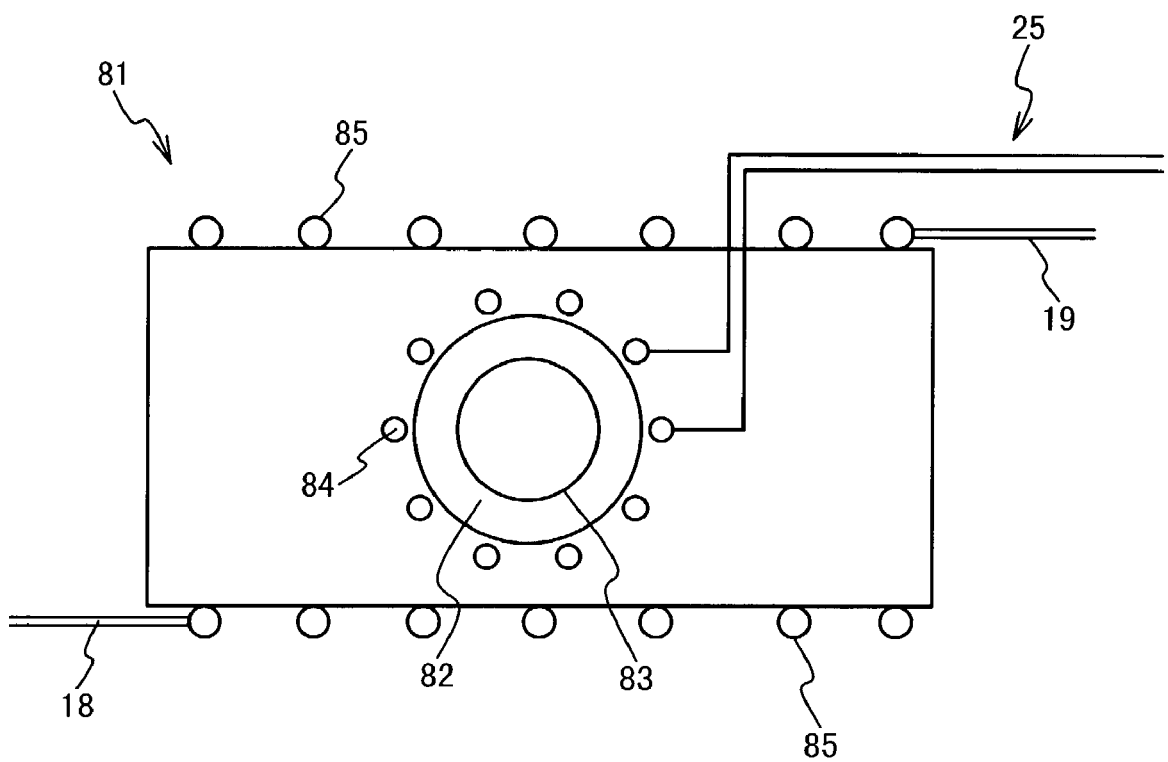
FIG. 10 is a diagram showing the structure of a furnace 81 used in the sixth embodiment of the present invention.

First, a furnace 81 shown in FIG. 10 is used instead of the cultivation vessel 2. The raw material for forming a sphere is housed inside the furnace 81. The detail of the furnace 81 is mentioned later.

Second, a cooling water as a thermal medium instead of the culture fluid is accommodated in the tank 3 shown in FIG. 1. Also, a cooling function to cool the cooling water is given to the tank 3. The cooling water accommodated in the tank 3 is supplied to the furnace 81 through the rotary joint 8 and the rotary joint 12 and cools the furnace 81. Also, the cooling water with the temperature increased by cooling the furnace 81 is returned to the tank 3 through the rotary joint 12 and the rotary joint 8. The returned cooling water is cooled by the tank 3 and is supplied to the furnace 81 again.

As shown in FIG. 10, the above-mentioned furnace 81 has a sphere material forming room 82. The raw materials 83 for forming the sphere material are put in the sphere material forming room 82. A heater 84 for heating the raw materials 83 is provided around the sphere material forming room 82. The heater 84 is connected with the above-mentioned electric cable 25. The electric power is supplied to the heater 84 from the control system 22 through the electric cable 23, the electric slip ring 10, the electric cable 24, the electric slip ring 14 and the electric cable 25.

Also, a water jacket 85 is provided for the furnace 81. The supply pipe 18 and the discharge pipe 19 are connected with the water jacket 85. As described above, the supply pipe 18 is connected with the tank 3 through the rotary joint 8 and the rotary joint 12. The supply pipe 18 supplies the cooling water accommodated in the tank 3 to water jacket 85. The water jacket 85 uses the supplied cooling water as the thermal medium and cools the furnace 81. The cooling water with the temperature increased by cooling the furnace 81 is discharged from the water jacket 85 by the discharge pipe 19. The discharge pipe 19 is connected with the tank 3 through the rotary joint 12 and the rotary joint 8 and returns the cooling water with temperature increased to the tank 3.

The sphere material forming apparatus in the sixth embodiment is used as follows and the sphere material as a target is formed. First, the raw materials 83 for forming a sphere are put in the sphere forming room 82 of the furnace 81. For example, as raw materials 83, glass can be used.

The electric power is supplied to the heater 84, and raw materials 83 are heated and melt by the heater 84. At this time, the raw materials 83 are heated and the furnace 81 is rotated around the 2 axes such that the melt raw materials 83 are stirred.

Subsequently, the cooling water is supplied and the raw materials 83 are gradually cooled. While being gradually cooled, the furnace 81 is rotated around the 2 axes and the direction of the gravity applied to the raw materials 83 is distributed 3-dimensionally. By setting the rotating frequency of the furnace 81 appropriately, the raw materials 83 become spherical and solidified and spherical material is formed. By distributing the direction of the applied gravity 3-dimensionally, the spherical material having the high uniformity is formed.

The sphere material forming apparatus in the sixth embodiment described above supplies the cooling water to the furnace 81 and the cooling water can be discharged from the furnace 81 in the rotation state of the furnaces 81 around the 2 axes and has the structure which is suitable to form the material of a sphere material.

It should be noted that in the sixth embodiment, the furnace 81 is rotated around the 2 axes but the furnace 81 can be rotated around two or more axes.

(Seventh Embodiment)

Figure 11:
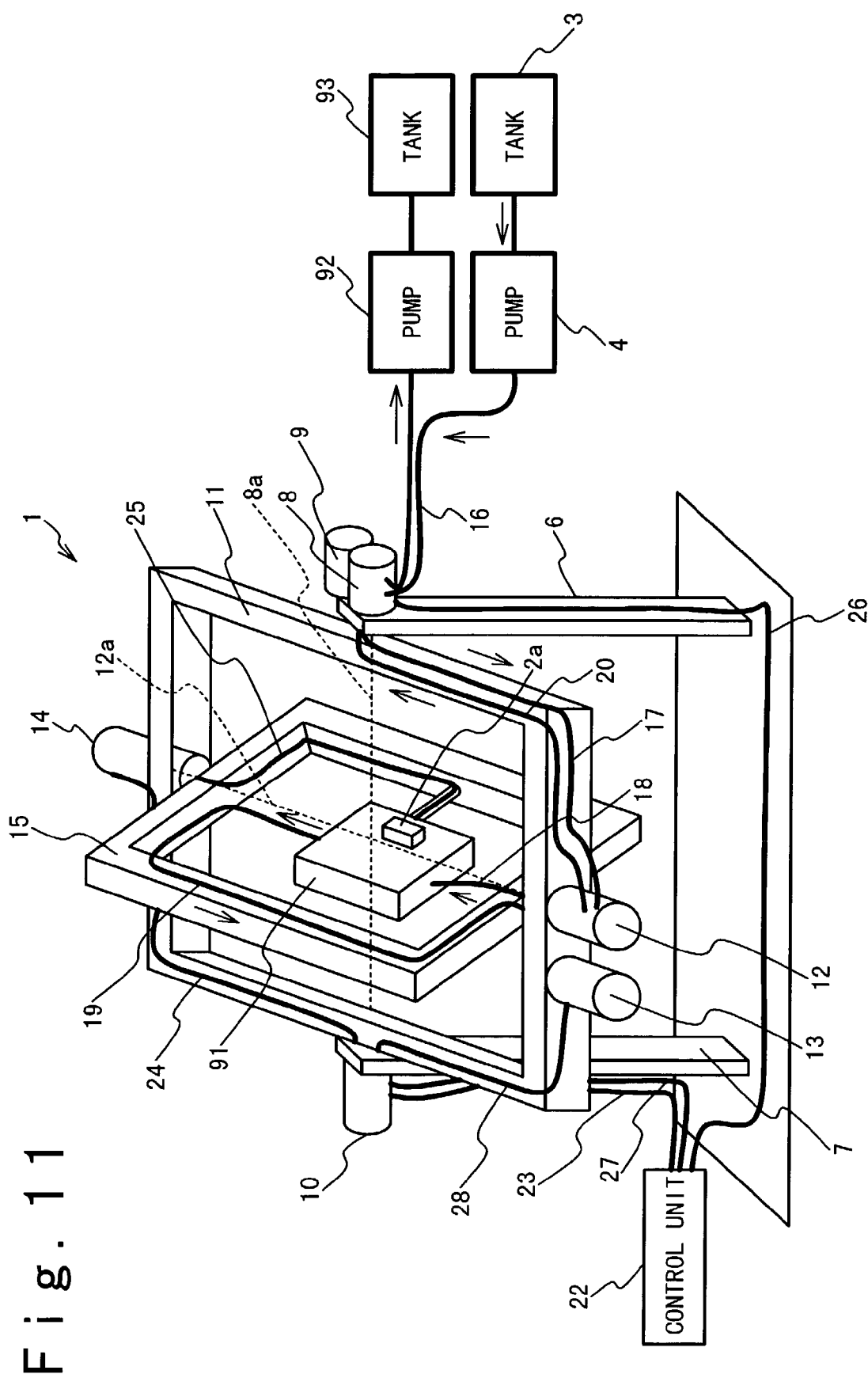
FIG. 11 is a diagram showing the structure of the 3-dimensional klinostat according to the seventh embodiment of the present invention.

The 3-dimensional klinostat according to the seventh embodiment of the present invention is used as a part of the material forming apparatus, as shown in FIG. 11. The material forming apparatus in the seventh embodiment has substantially the same structure as the cell lump cultivation apparatus in the first embodiment but differs from the first embodiment on the following points.

First, a reaction vessel 91 is used instead of the cultivation vessel 2. The raw materials for forming material are supplied to the reaction vessel. The raw materials react in a reaction vessel 91 and desired material is formed. The monitoring unit 2a is provided for the reaction vessel 91 and is used for the monitoring the state of reaction vessel 91.

Second, the raw materials to form material are accommodated in the tank 3. The raw materials are accommodated in the tank 3 are fluid and may be any of liquid and gas.

Third, the discharge pipe 21 is not connected with the tank 3 but the pump 92. The pump 92 is connected with the tank 93. The reaction vessel 91 is connected with the reaction vessel 91 through the discharge pipe 19, the rotary joint 12, the discharge pipe 20, the rotary joint 8 and the discharge pipe 21. The pump 91 sends the reaction product generated in the reaction vessel 91 to the tank 93 with a pressure. The reaction product sent to the tank 93 is fluid and may be either liquid or gas.

The raw materials accommodated in the tank 3 are sent to the pump 4 with the pressure and are supplied to the reaction vessel 91 through the rotary joints 8 and 12. The reaction vessels 91 are rotated around the 2 axes. The raw materials react in the reaction vessel 91 rotated around the 2 axes in the state in which the gravity is applied 3-dimensionally and generates the reaction product. The generated reaction product is discharged from the reaction vessel 91 to the tank 93 through the rotary joints 8 and 12. By controlling the operation timings of the pump 4 and the pump 92, the reaction vessel 91 can be supplied with the raw materials in the optional timing. Also, the reaction product can be discharged from the reaction vessel 91.

In the material forming apparatus in the seventh embodiment described above, the raw materials are supplied to the reaction vessel 91 in the rotation state of the reaction vessel 91 around the 2 axes and the reaction product can be discharged from the reaction vessel 91. Therefore, the material forming apparatus in the seventh embodiment has the desired structure to form material in the state in which the gravity is applied 3-dimensionally.

In the present invention, the 3-dimensional klinostat is provided in which a sample can be rotated around two or more axes and it is possible to supply fluid to a sample in the rotation state of the sample.

Also, according to the present invention, the cell lump cultivation apparatus is provided in which the cultivation vessel for storing a cell lump can be rotated around two or more axes and it is possible to supply the culture fluid to the cell lump cultivation in the rotation state of the cultivation vessel.

Also, according to the present invention, the cell lump cultivation apparatus is provided in which the cultivation vessel for storing a cell lump can be rotated around two or more axes and make it possible to cultivate the cell lump for a long term.

Also, according to the present invention, the organism growing apparatus is provided in which the growth vessel for accommodating an organism can be rotated around two or more axes and it is possible to supply the substances necessary to grow the organism to the organism to be grown in the rotation state of the growth vessel.

Also, according to the present invention, the material forming apparatus is provided in which the vessel for accommodating the materials can be rotated around two or more axes and it is possible to supply the raw material in fluid or thermal medium in fluid in the rotation state of the growth vessel.

What is claimed is:

1. An application apparatus of a klinostat, comprising:
   a vessel in which an object is encapsulated;
   a rotating unit which rotates said vessel around n axes (n is an integer more than 1) such that gravity is equally applied to said object;
   a fluid supply unit which supplies fluid into said vessel, while said vessel is rotated wherein said object is a cell lump, and said cell lump and said fluid being encapsulated in said vessel; said cell lump is adhered to an artificial matrix, and wherein said fluid, said artificial matrix, and a supporting section for supporting said artificial matrix are encapsulated in said vessel.

2. The application apparatus according to claim 1, wherein said fluid contains an agent to promote differentiation of said cell lump.

3. The application apparatus according to claim 1, wherein a coefficient of viscosity of said fluid is adjusted such that said cell lump does not touch said vessel.

4. The application apparatus according to claim 1, wherein said fluid supply unit circulates said fluid.

5. The application apparatus according to claim 1, wherein said fluid supply unit dumps said fluid.

6. The application apparatus according to claim 1, wherein said fluid supply unit has a function to adjust a concentration of at least a gas contained in said fluid.

7. The application apparatus according to claim 1, wherein said support section has a pipe functioning as a vein.

8. The application apparatus according to claim 1, wherein said vessel comprises:
   a first room to which said fluid is supplied from said fluid supply unit;
   a second room in which said object is capsulated; and
   a separation member which has a plurality of holes and is provided for separation of said first and second rooms, said fluid in said first room and said fluid in said second room are exchanged through said plurality of holes.

9. A cell cultivation apparatus comprising:
   a cultivation vessel which accommodates a cultivation cell lump;
   a rotating unit which rotates said cultivation vessel around n axes (n is an integer more than 1);
   a culture fluid supply unit which supplies culture fluid from a stationary system to the cultivation vessel in a rotation state of said cultivation vessel around the n axes; and
   wherein said cultivation vessel accommodates an artificial matrix to which said cultivation cell lump are adhered.

10. The cell cultivation apparatus according to claim 9, wherein said artificial matrix is fixed on said cultivation vessel.

11. The cell cultivation apparatus according to claim 9, wherein the artificial matrix contains an artificial matrix pipe, and
    said culture fluid supply unit supplies said culture fluid through artificial matrix pipe.

12. The cell cultivation apparatus according to claim 9, further comprising:
    a culture fluid tank which accumulates said culture fluid discharged from said cultivation vessel,
    wherein said culture fluid supply apparatus takes out said culture fluid from said culture fluid tank and supplies to the cultivation vessel.

13. The cell cultivation apparatus according to claim 9, further comprising:
    a material concentration adjusting unit which controls a concentration of a material contained in said culture fluid.

14. The cell cultivation apparatus according to claim 9, wherein said cultivation vessel comprises:
    a supply pipe through which said culture fluid is supplied from said culture fluid supply unit;
    a first room which is connected with a discharge pipe through which said culture fluid is discharged; and
    a second room which is separated from said first room by a separation member for which holes are provided to pass said culture fluid and holds said cultivation cell lump in said culture fluid.

15. The cell cultivation apparatus according to claim 9, wherein said rotating unit comprises:
    a first member which supports said cultivation vessel;
    a first rotary joint which supports said first member rotatably around a first rotation axis;
    a first rotating unit which rotates said first member around the first rotation axis;
    a second member which supports said first rotary joint;

a second rotary joint which supports said second member rotatably around a second rotation axis which is not parallel to the first rotation axis; and a second rotating unit which rotates said second member around the second rotation axis, wherein said culture fluid supply unit supplies said culture fluid to the cultivation vessel through said first rotary joint and said second rotary joint.

16. A cell sample forming apparatus comprising:

a cultivation vessel which accommodates a cell;

a rotating unit which rotates said cultivation vessel around n axes (n is an integer more than 1); and a fixation liquid supply unit which supplies fixation liquid from a stationary system to said cultivation vessel to fix the cell or a gene of the cell, in a rotation state of said cultivation vessel around the n axes.

* * * * *